United States Patent [19]

Bobst et al.

[11] Patent Number: 5,788,699

[45] Date of Patent: Aug. 4, 1998

[54] DRILL SECTION, AS WELL AS KIRSCHNER WIRES, BONE ROUTERS AND THE LIKE EQUIPPED WITH SUCH A DRILL SECTION

[75] Inventors: Frank Bobst, Oensingen, Switzerland; Peter Griss, Marburg, Germany

[73] Assignee: Endocare AG, Switzerland

[21] Appl. No.: 624,381

[22] PCT Filed: Jun. 20, 1994

[86] PCT No.: PCT/EP94/02009

§ 371 Date: Nov. 6, 1996

§ 102(e) Date: Nov. 6, 1996

[87] PCT Pub. No.: WO95/09569

PCT Pub. Date: Apr. 13, 1995

[30] Foreign Application Priority Data

Mar. 18, 1993 [DE] Germany ............... 94 04 630.1
Oct. 4, 1993 [DE] Germany ............... 43 33 755.4

[51] Int. Cl.[6] .................................................. A61B 17/16
[52] U.S. Cl. ........................... 606/80; 408/227; 408/229
[58] Field of Search ............................. 606/59, 79, 80; 408/227, 228, 229

[56] References Cited

U.S. PATENT DOCUMENTS

| 385,088 | 6/1888 | Benzie ................................ 408/227 |
| 2,981,127 | 4/1961 | Ransom ............................... 408/229 |
| 4,341,206 | 7/1982 | Perrett et al. ........................ 606/80 |
| 4,373,518 | 2/1983 | Kaiser et al. ........................ 606/72 |

FOREIGN PATENT DOCUMENTS

| 2552694 | 4/1985 | France . |
| 9101385 | 6/1991 | Germany . |
| WO94/12107 | 6/1994 | WIPO . |

*Primary Examiner*—Michael Buiz
*Assistant Examiner*—David O. Reip
*Attorney, Agent, or Firm*—Andrus, Sceales, Starke & Sawall

[57] ABSTRACT

A medical drill for drilling holes in a bone or cartilage is formed with an end drill section. The end drill section has a specially formed drill tip at the distal end. The drill tip includes a flattened section which is located diametrically in relation to the central axis of the drill. The drill may be formed on the end of a router to provide a single loop to drill a pilot hole and then continue with the routing process. The drill section minimizes the heat created within the bone or cartilage.

5 Claims, 2 Drawing Sheets

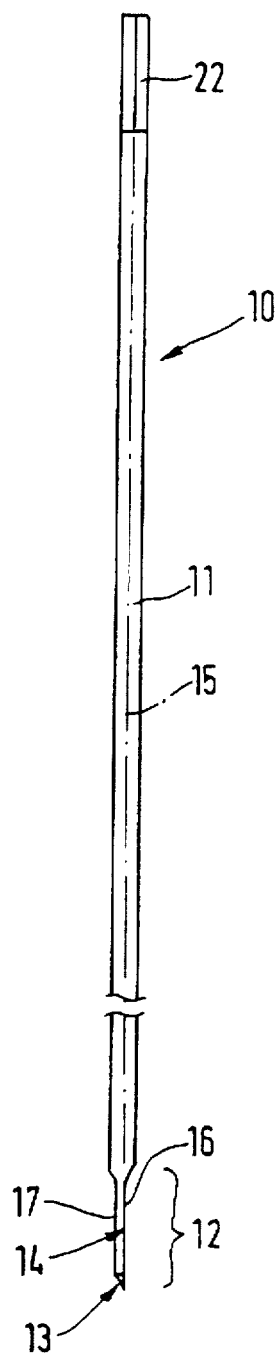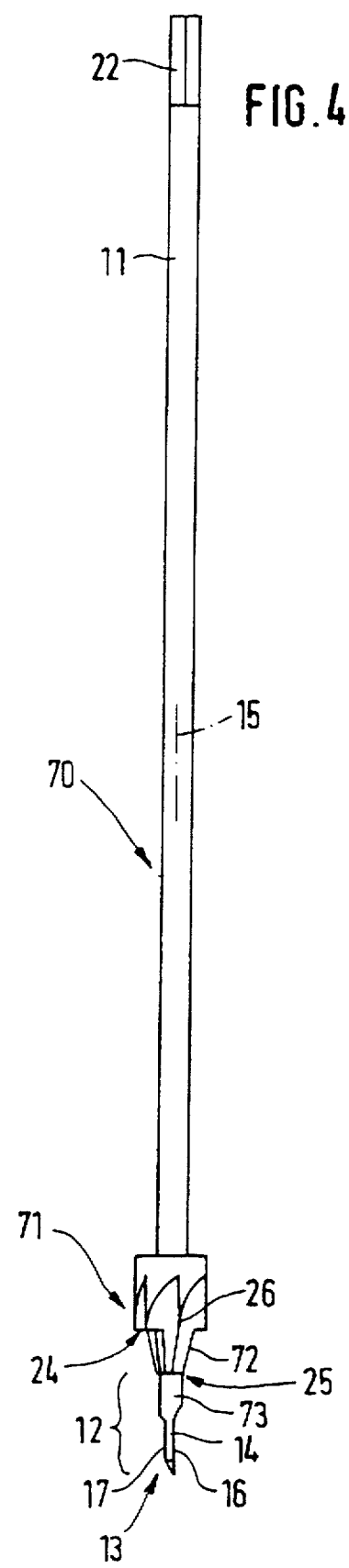

DRILL SECTION, AS WELL AS KIRSCHNER WIRES, BONE ROUTERS AND THE LIKE EQUIPPED WITH SUCH A DRILL SECTION

BACKGROUND OF THE INVENTION

The invention relates to a drill section of a medical drill rod including a Kirschner wires, bone routers, bone drills or the like equipped with a shaft and drill section.

In various medical applications it is necessary to make a hole in a bone. For this purpose it is customary to equip diverse tools with drill sections, which serve to produce a hole of this kind.

For example, the use of a drill section as mentioned above in combination with a so-called Kirschner wire is known. Kirschner wires—also known as bone-transfixion wires— are employed particularly in cases of wire extension in association with an external fixation device. Wire extension is a method of adjusting displaced ends of a fracture by overcoming the opposed pulling force of a muscle. The extension is achieved by loading with variable weights steel wires, namely so-called Kirschner wires, that have been drilled through the bone and arranged in a frame so that tension is maintained.

However, bone drills are also of special importance when routing tools are used to produce openings and cavities in bone, in particular during the creation of spaces for implantation. The reason is that care must be taken to define precisely the implantation space to be created in the bone. For this purpose it is customary first to drill a pilot hole with a separate drill. Then the bone router is centered in the pilot hole and used for further excavation.

Conventional drill sections, most of which employ a conical drill tip, have the disadvantage that during drilling at a speed of 1200 to 2000 rpm the bone is heated, reaching temperatures up to 120° in the drilling region. Such temperatures cause deterioration and destruction, in particular charring, of the bone or bony tissue in the region of the drilled hole.

SUMMARY OF THE PRESENT INVENTION

It is the object of the present invention to create a drill section with which a hole can be made in a bone with no deterioration of the remainder of the bone or the remaining bony tissue.

This object is achieved by a drill section proximate to the drill tip which is flattened diametrically relative to the central axis (15) of the drill section.

One characteristic of the drill section essential to the invention is the diametrically flattened drill section. Experiments have shown that with such a configuration of the drill section, especially when the diametric flattening extends into the drill tip so that the latter forms a section shaped like part of a cone, even when the drill rotates at speeds of 1200 to 2000 rpm the temperature at the drill tip is maximally about 50°–60° C. As a result charring and the associated deterioration of the bone during the creation of a hole are effectively prevented.

For removal of the chips of bone it is particularly significant that the one flat side, which defines the cutting edge, extends in the region of the central axis of the shaft, whereas the opposite flat side is spaced slightly apart from the central axis of the shaft.

To achieve minimal temperatures at the drill tip, the latter preferably tapers at an angle of at most about 55°–65°, in particular about 60°. If this angle is outside this range on either side, either the drill section becomes less efficient or higher temperatures are produced at the drill tip.

It is also advantageous regarding the reduction of temperature at the drill tip for the surface of the drill tip to be polished smooth.

The proximal end of the shaft of a Kirschner wire or the like provided with a drill section of the stated kind comprises a surface or a section with triangular or polygonal cross section, so that it transmits torque when attached to a drilling machine or a hand lever or the like.

It is particularly advantageous when the drill section in accordance with the invention is combined with a routing tool, in particular a cartilage or bone router. As described above, to create implantation spaces it is customary first to drill pilot holes, in which the routing tools are then centered and operated. However, with this procedure the precision suffers, as does the bone itself. In a special embodiment of the invention, a cylindrical routing element is disposed adjacent to the drill section. With such a tool the drilling of a pilot hole and the excavation of the bone can be carried out as a single process. The effect is to ensure that the implantation space is created with high precision. Moreover, the various steps are combined into a single successive operation. In this regard it should be noted especially that the drilling of a pilot hole and the routing can also be carried out as a single operation with a drill section not constructed as described above. For this reason a cartilage or bone router is disclosed, in which a cylindrical routing element is disposed near the distal end of a rodlike shaft, the shaft continues distally beyond the routing element, and a drill section is formed at this continuation of the shaft.

In addition, it is advantageous for a routing element in the shape of a truncated cone to be disposed distal to the cylindrical routing element. A tool so constructed is suitable for producing holes in vertebrae to receive so-called tulip screws. In connection with a so-called "internal fixation device", the said screws are so-called transpedicular screws. Preferably such screws include a section shaped like a truncated cone between the threaded section and the tulip-shaped screw head; this middle section, in cooperation with a correspondingly shaped receiving space in the bone, ensures extremely high stability of the bone screw. It should be kept in mind here that the conical section of the screw acts in the region of the hard, cortical bone. With this embodiment, the threaded section of the bone screw need no longer absorb any lateral forces.

BRIEF DESCRIPTION OF THE DRAWINGS

In the following an embodiment of a drill section constructed in accordance with the invention is described in detail, alone and in connection with a Kirschner wire and bone router, with reference to the attached drawings, wherein:

FIG. 3 is a schematic drawing of a Kirschner wire, at the distal end of which a drill section according to FIGS. 1 and 2 is disposed; and FIG. 4 is a schematic drawing of a cartilage and bone router, at the distal end of which a drill section according to FIGS. 1 and 2 is disposed.

DESCRIPTION OF THE ILLUSTRATED EMBODIMENT

Figure 1:
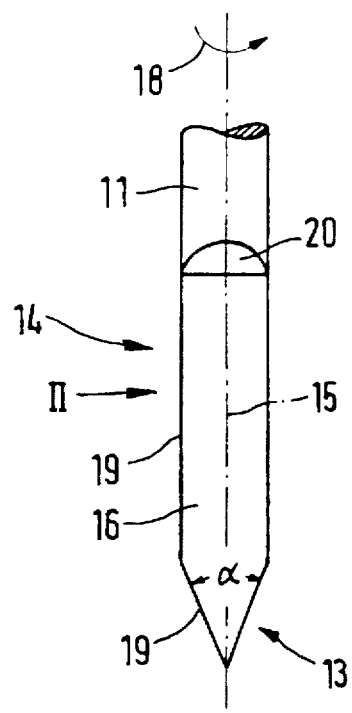
FIG. 1 shows an enlarged partial section of an embodiment of a drill section, in side view.
Figure 2:
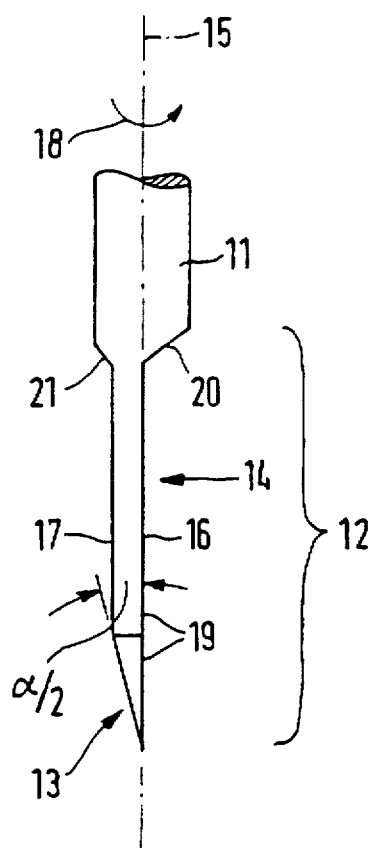
FIG. 2 shows an enlarged partial section of the drill section according to FIG. 1 as viewed in the direction II in FIG. 1.

The drill section shown in FIGS. 1 and 2 comprises a shaft 11 in the form of a round rod, at the distal end of which a drill tip 13 is disposed, forming the distal end of a section 14 that is flattened diametrically relative to the central axis 15 of the shaft. The two flat sides thus formed are identified by the reference numerals 16 and 17. The one flat side 16 extends in the region of the central axis 15 of the shaft, whereas the opposite flat side 17 is spaced apart from the central axis 15. The one flat side 16 shown in FIG. 2, which also defines the cutting edge 19, extends through the central axis 15 of the shaft. The drill tip 13 corresponding to FIG. 2 is thus the apex of a cone flattened on one side.

The flat side 16 is preferably spaced slightly apart from the central axis 15 of the shaft, in such a way that it is on the opposite side of the central axis from the flat side 17. Its distance from the central axis is about 3/100–8/100 mm, in particular about 5/100 mm. This slight displacement from the central axis has proved especially advantageous with respect to the cutting action. The cutting edge 19 is scarfed. In the embodiment shown here, the drill section is turned counterclockwise (arrow 18 in FIGS. 1 and 2) through the bone. Accordingly, the cutting edge 19 is the leading edge of the flat side 16 that extends to the drill tip. Preferably, the opposite edge of the flat side 16 is also scarfed, so that the drill section can also be used when attached to a motor that rotates clockwise. The drilling machine customarily used is a compressed-air machine with a speed of 1200 to 2000 rpm.

As explained above, regarding the temperature generated during drilling it is advantageous if the drill tip 13 tapers at a (solid) angle α of about 55° to 65°, in particular about 60°. Angles in this range have proved optimal with respect to both an optimal efficiency of drilling on one hand, and low heat production on the other.

The surface of the drill tip 13 is preferably polished smooth, as are the other parts of the drill section 12.

The slanted surfaces at the transition between the flat sides 16, 17 of the drill section 12 or the section 14 on one hand and the shaft 11 on the other hand are identified by the reference numerals 20 and 21. As can be seen in FIG. 3, these transitional surfaces 20, 21 each slant towards the drill tip 13. This inclination is made such as to ensure that bone chips will be reliably guided outward during drilling through the bone. Preferably the transitional surface 20 adjacent to the flat side 16 is hollowed out to form a channel, in particular has the shape of a quadrant of a circle.

In the present exemplary embodiment, the length of the drill section is between 5 and 30 mm, in particular about 10 to 25 mm. In the extreme case it can be as great as 50–60 mm, with a shaft diameter of about 1.5 to 8 mm. The smaller the shaft diameter is, the less is the length of the drill section 12. With a shaft diameter of 1.8 mm, the length of the drill section 12 is about 7 mm. With a shaft diameter of 3 mm, the length of the drill section 12 is about 25 mm, whereas with a shaft diameter of 5 to 8 mm, the drill section 12 is about 50 mm long.

The thickness of the flattened end (in this exemplary embodiment) is between 1.0 and 2.5 mm. The thickness of the section 14 increases corresponding to the diameter of the shaft 11; i.e., with a shaft diameter of 1.8 mm the thickness of the flattened section 14 is about 0.8 mm, whereas with a shaft diameter of 8 mm the thickness of the flattened section 14 is about 2.4 mm.

Optimal results with respect to temperature and the removal of bone chips are obtained with the following values of shaft diameter D, length L of the drill section 12 and thickness W of the flattened section 14:

| (a) | D = 3   | mm |
|     | L = 25  | mm |
|     | W = 1.2 | mm |
| (b) | D = 1.8 | mm |
|     | L = 7   | mm |
|     | W = 0.8 | mm |
| (c) | D = 5   | mm |
|     | L = 50  | mm |
|     | W = 1.6 | mm |
| (d) | D = 4   | mm |
|     | L = 30  | mm |
|     | W = 1.5 | mm |

The angle α in all the above examples is 60°.

In FIG. 3 the drill section described in FIGS. 1 and 2 is shown in combination with a Kirschner wire 10. Here the shaft 11 in the form of a round rod is long, forming the Kirschner wire 10. The shaft 11 at the distal end of the Kirschner wire 10 is shaped as described above to form a drill section. At the proximal end of the Kirschner wire 10 or the shaft 11 is a surface or a section 22 with a triangular or polygonal, here square cross section, for torque-transmitting connection to a drilling machine or a hand lever, not shown here.

If the shaft 11 is not made as long as in the case of a Kirschner wire, the preceding construction produces a bone drill having the same good drilling properties as with the Kirschner wire.

Another application of the drill section can be seen in FIG. 4. In this drawing a bore section is shown schematically in combination with a cartilage or bone router 70, which is particularly suitable for producing corresponding implantation spaces in a vertebral bone. The cartilage or bone router 70 again comprises a shaft 11 in the form of a round rod, at the distal end of which a drill section according to FIGS. 1 and 2 is disposed. Betwen drill section and shaft is a cylindrical routing element 71.

In the embodiment according to FIG. 4 there is disposed distal to the cylindrical routing element 71 a routing element 72 in the form of a truncated cone. The latter serves to create a correspondingly conical part of a hole in the bone, into which can be set a correspondingly shaped bone screw. Between the conical routing element 72 and the drill section is a shaft section 73, the length of which is about half the length of the section 14. This shaft section 73 serves to guide the router during drilling and subsequent routing. The proximal end of the shaft 11 again, as in the preceding exemplary application, comprises a surface or a section 22 with triangular or polygonal cross section for torque-transmitting connection to a drilling machine or hand lever.

According to the exemplary embodiment shown in FIG. 4, the length of the section 14 is approximately equal to the length of the cylindrical routing element 71. The routing element 72 in the shape of a truncated cone has a length about half that of the cylindrical routing element 71. These dimensions are chosen to correspond to preferred dimensions of transpedicular vertebral screws.

Between the cylindrical routing element 71 and the conical routing element 72 there is formed a shoulder 24 that extends radially inward over the circumference. A corresponding shoulder 25 is situated between the conical routing element 72 and the shaft section 73. The conical routing element 72 tapers toward the drill tip 13. The cutting edges of the cylindrical and conical routing elements are identified by the reference numeral 26.

All the characteristics disclosed in the application documents are claimed as essential to the invention, to the extent that they are new to the state of the art singly or in combination.

We claim:

1. A drill section for a bone drilling end of a surgical instrument, comprising:

a round shaft portion at a proximal end; and a flattened drilling portion at a distal end, said drilling portion comprising a first flat surface and an opposing second flat surface; wherein said first flat surface is diametrically located relative to a central longitudinal axis of said shaft portion and forms diametrically opposed and parallel outer cutting edges for drilling, and wherein said second flat surface is parallel to said first flat surface and is radially offset from said central longitudinal axis.

2. The drill section of claim 1, wherein said drilling portion further comprises a conically tapered drill tip portion, and wherein the first flat surface extends onto the drill tip portion so that the drill tip portion has the shape of a cone flattened on one side.

3. The drill section of claim 2, wherein the drill tip portion is tapered at an angle within the range of about 55–65 degrees.

4. The drill section of claim 1, wherein said drill section is formed as a bone drilling end of a Kirschner wire.

5. The drill section of claim 1, wherein said drill section is formed as a bone drilling end of a bone router.

* * * * *